United States Patent
Gonçalves Dos Reis et al.

(10) Patent No.: US 11,998,665 B2
(45) Date of Patent: *Jun. 4, 2024

(54) BIODEGRADABLE URETERAL STENTS, METHODS AND USES THEREOF

(71) Applicant: ASSOCIATION FOR THE ADVANCEMENT OF TISSUE ENGINEERING AND CELL BASED TECHNOLOGIES & THERAPIES (A4TEC), Braga (PT)

(72) Inventors: Rui Luis Gonçalves Dos Reis, Oporto (PT); Ana Rita Cruz Duarte, Braga (PT); Alexandre António Antunes Barros, Braga (PT); Estêvão Augusto Rodrigues De Lima, Oporto (PT); Carlos André Ribeiro Oliveira, Guimarães (PT)

(73) Assignee: ASSOCIATION FOR THE ADVANCEMENT OF TISSUE ENGINEERING AND CELL BASED TECHNOLOGIES & THERAPIES (A4TEC)—ASSOCIAÇÃO, Braga (PT)

( * ) Notice: Subject to any disclaimer, the term of this patent is extended or adjusted under 35 U.S.C. 154(b) by 1668 days.

This patent is subject to a terminal disclaimer.

(21) Appl. No.: 16/084,059

(22) PCT Filed: Mar. 13, 2017

(86) PCT No.: PCT/IB2017/051448
§ 371 (c)(1),
(2) Date: Sep. 11, 2018

(87) PCT Pub. No.: WO2017/153973
PCT Pub. Date: Sep. 14, 2017

(65) Prior Publication Data
US 2020/0230299 A1    Jul. 23, 2020

(30) Foreign Application Priority Data

Mar. 11, 2016 (PT) .......................................... 109229

(51) Int. Cl.
*A61L 31/00* (2006.01)
*A61F 2/04* (2013.01)
(Continued)

(52) U.S. Cl.
CPC .............. *A61L 31/148* (2013.01); *A61F 2/04* (2013.01); *A61K 31/337* (2013.01);
(Continued)

(58) Field of Classification Search
CPC ........ A61L 31/148; A61L 31/16; A61L 31/10; A61L 31/042; A61L 31/041; A61L 31/18;
(Continued)

(56) References Cited

U.S. PATENT DOCUMENTS 11,000,633 B2 *  5/2021  Gonçalves Dos Reis ..................
                                                        A61L 31/041
2006/0246108 A1   11/2006  Pacetti
(Continued)

FOREIGN PATENT DOCUMENTS

EP          0420541        4/1991
WO      2016/181371 A1    11/2016

OTHER PUBLICATIONS

Fan et al. Preparation and characterization of alginate/gelatin blend fibers. Journal of Applied Polymer Science, 96(5), pp. 1625-1629. (Year: 2005).*

(Continued)

*Primary Examiner* — Suzette J Gherbi
(74) *Attorney, Agent, or Firm* — Leason Ellis LLP

(57) ABSTRACT

The present disclosure relates to biodegradable ureteral stents comprising an anti-cancer drug, and to a composition
(Continued)

for use in medicine that may be used to ensure patency of a channel, namely a mammal ureter, for example, an obstructed ureter by a urinary stone, neoplasia or by a surgical procedure. The biodegradable ureteral stents (BUS) disclosed in the present disclosure unexpectedly allow a proper release of anti-cancer drugs, thus extending the duration of the treatment and increasing the efficacy of the treatment.

18 Claims, 9 Drawing Sheets

(51) Int. Cl.
    *A61K 31/337*    (2006.01)
    *A61K 31/704*    (2006.01)
    *A61K 31/7068*    (2006.01)
    *A61K 47/36*    (2006.01)
    *A61K 47/42*    (2017.01)
    *A61L 31/04*    (2006.01)
    *A61L 31/14*    (2006.01)
    *A61L 31/16*    (2006.01)
    *A61L 31/18*    (2006.01)
(52) U.S. Cl.
    CPC ........ *A61K 31/704* (2013.01); *A61K 31/7068* (2013.01); *A61K 47/36* (2013.01); *A61K 47/42* (2013.01); *A61L 31/041* (2013.01); *A61L 31/16* (2013.01); *A61L 31/18* (2013.01); *A61F 2002/048* (2013.01); *A61L 2300/416* (2013.01)
(58) Field of Classification Search
    CPC ................. A61L 2300/416; A61F 2/04; A61F 2002/048; A61K 31/337; A61K 31/704; A61K 47/42; C08L 67/04; C08L 69/00; C08L 5/04; C08L 83/06
    See application file for complete search history.

(56) References Cited

U.S. PATENT DOCUMENTS

2013/0331927 A1* 12/2013 Zheng ....................... A61F 2/90
    623/1.19
2018/0296734 A1* 10/2018 Gonçalves Dos Reis ...................
    A61P 35/00
2021/0275472 A1* 9/2021 Pathak ................. A61K 9/1641

OTHER PUBLICATIONS

Lammers et al. Simultaneous delivery of doxorubicin and gemcitabine to tumors in vivo using prototypic polymeric drug carriers. Biomaterials, 30(20), pp. 3466-3475. (Year: 2009).*
Yoda et al. Impregnation of paclitaxel into poly(dl-lactic acid) using high pressure mixture of ethanol and carbon dioxide. RSC Advances, 1(1), p. 156. (Year: 2011).*
Barros Alexandre A et al., "Ketoprofen-eluting biodegradable ureteral stents by CO2impregnation: In vitro study", International Journal of Pharmaceutics, (Sep. 21, 2015), vol. 495, No. 2, , ISSN 0378-5173, pp. 651-659, 2015.
Shaikh Mohsin et al., "Non-vascular drug eluting stents as localized controlled drug delivery platform: Preclinical and clinical experience", Journal of Controlled Release, (Aug. 17, 2013), vol. 172, No. 1,2013, pp. 105-117.
Alexandre A. Barros et al., "Bioresorbable ureteral stents from natural origin polymers", Journal of Biomedical Materials Research. Part B: Applied Biomaterials, US, (Jun. 26, 2014), vol. 103, No. 3, doi:10.1002/jbm.b.33237, ISSN 1552-4973, pp. 608-617.
Dirk Lange et al., "Ureteral stent-associated complications where we are and where we are going", Nature Reviews. Urology, US, (Dec. 23, 2014), vol. 12, No. 1, doi:10.1038/nrurol.2014.340, ISSN 1759-4812, pp. 17-25.
Aroso, I.M; Craveiro, R.; Rocha, A.; Dionisio, M.; Barreiros, S.; Reis, R.L.; Paiva, A.; Duarte, A.R.C., "Design of controlled release systems for THEDES-Therapeutic deep eutectic solvents, using supercritical fluid technology", Int. J. Pharm., (2015), vol. 492, doi:doi:10.1016/j.ijpharm.2015.06.038, pp. 73-79, XP029258597.
Audenet, F.; Traxer, O.; Bensalah, K.; Roupret, M., "Upper urinary tract instillations in the treatment of urothelial carcinomas: A review of technical constraints and outcomes", World J. Urol, (2013), vol. 31, pp. 45-52.
Audenet, F.; Yates, D.R.; Cussenot, O.; Roupret, M., "The role of chemotherapy in the treatment of urothelial cell carcinoma of the upper urinary tract (UUT-UCC", Urol. Oncol., (2013), vol. 31, pp. 407-413.
Babjuk, M.; Burger, M.; Zigeuner, R.; Shariat, S.F.; Van Rhijn, B.W.G.; Comperat, E.; Sylvester, R.J.; Kaasinen, E.; Bohle, A.; PA, "EAU guidelines on non-muscle-invasive urothelial carcinoma of the bladder: update 2013", Eur. Urol., (2013), vol. 64, pp. 639-653.
Barros, A.A.; Oliveira, C.; Reis, R.L.; Lima, E.; Duarte, A.R.C., "Ketoprofen-eluting biodegradable ureteral stents by C02 impregnation: In vitro study", Int. J. Pharm., (2015), vol. 495, doi:doi:10.1016/j.ijpharm.2015.08.040, pp. 651-659, XP029292185.
Barros, A.A.; Rita, A.; Duarte, C.; Pires, R.A.; Sampaio-Marques, B.; Ludovico, P.; Lima, E.; Mano, J.F.; Reis, R.L., "Bioresorbable ureteral stents from natural origin polymers", J. Biomed. Mater. Res. Part B Appl. Biomater., (2015), vol. 103, doi:doi:10.1002/jbm. b.33237, pp. 608-617, XP055223832.
Berens, A.R; Huvard, G.S.; Korsmeyer, R.W.; Kunig, F.W., "Application of compressed carbon dioxide in the incorporation of additives into polymers", J. Appl. Polym. Sci., (1992), vol. 46, pp. 231-242.
Browne, S.; Fontana, G.; Rodriguez, B.J.; Pandit, A., "A protective extracellular matrix-based gene delivery reservoir fabricated by electrostatic charge manipulation", Mol. Pharm., (2012), vol. 9, pp. 3099-3106.
Browne, S.; Pandit, A., "Multi-modal delivery of therapeutics using biomaterial scaffolds", J. Mater. Chem. B, (2014), vol. 2, pp. 6692-6707.
Champeau, M.; Thomassin, J.- M.; Tassaing, T.; Jerome, C., "Drug Loading of Sutures by Supercritical C02 Impregnation: Effect of Polymer", Drug Interactions and Thermal Transitions. Macromol. Mater. Eng., (2015), vol. 300, doi:doi:10.1002/mame.201400369, pp. 596-610, XP055193663.
Cooper, A.I., "Polymer synthesis and processing using supercritical carbon dioxide", J. Mater. Chem., (2000), vol. 10, doi:doi: 10.1039/a906486i, pp. 207-234, XP055112373.
D.; L.; M.; M.; M.; K.; M.; S., "Hydrogel based drug retention system for the treatment of upper tract urothelial carcinoma", Eur. Urol., (2014), vol. 13, pp. E25-E25A.
Elvira, C.; Fanovich, A.; Fern ??ndez, M.; Fraile, J.; San Rom ??N, J.; Domingo, C., "Evaluation of drug delivery characteristics of microspheres of PMMA-PCL-cholesterol obtained by supercritical-CO 2 impregnation and by dissolution-evaporation techniques", J. Control. Release, (2004), vol. 99, doi:doi:10.1016/j.jconrel.2004. 06.020, pp. 231-240, XP004569544.
Hadaschik, B.A.; Ter Borg, M.G.; Jackson, J.; Sowery, R.D.; So, A.I.; Burt, H.M.; Gleave, M.E., "Paclitaxel and cisplatin as intravesical agents against non-muscle-invasive bladder cancer", BJU INT., (2008), vol. 101, pp. 1347-1355.
Hellenthal, N.J.; Shariat, S.F.; Margulis, V.; Karakiewicz, P.I.; Roscigno, M.; Bolenz, C.; Remzi, M.; Weizer, A.; Zigeuner, R.; B, "Adjuvant chemotherapy for high risk upper tract urothelial carcinoma: results from the Upper Tract Urothelial Carcinoma Collaboration", J. Urol., (2009), vol. 182, pp. 900-906, XP026447990.
Jiao, Z.; Chen, Z.; Wu, Y.; Ma, S., "Determination of Paclitaxel Solubility in Carbon Dioxide Using Quartz Crystal Microbalance", Chinese J. Chem. Eng., (2011), vol. 19, pp. 227-231.
Kazarian, S.G., "Polymer Processing with Supercritical Fluids", Polym. Sci., (2000), vol. 42, pp. 78-101, XP002739176.

(56) References Cited

OTHER PUBLICATIONS

Kazarian, S.G.; Martirosyan, G.G., "Spectroscopy of polymer/drug formulations processed with supercritical fluids: in situ ATR-IR and Raman study of impregnation of ibuprofen into PVP", Int. J. Pharm., (2002), vol. 232, doi:doi:10.1016/S0378-5173(01)00905-X, pp. 81-90, XP027429878.

Khan, W.; Farah, S.; Domb, A.J., "Drug eluting stents: developments and current status", J. Control. Release, (2012), vol. 161, doi:doi:10.1016/j.jconrel.2012.02.010, pp. 703-712, XP028492695.

Kikic, I .; Sist, P., Applications of Supercritical Fluids to Pharmaceuticals: Controlled Drug Release Systems BT—Supercritical Fluids: Fundamentals and Applications, Springer Netherlands, (2000), pp. 291-306.

Kikic, I.; Vecchione, F., "Supercritical impregnation of polymers", Curr. Opin. Solid State Mater. Sci., (2003), vol. 7, doi:doi:10.1016/j.cossms.2003.09.001, pp. 399-405, XP055131937.

Krambeck, A.E.; Walsh, R.S.; Denstedt, J.D.; Preminger, G.M.; Li, J.; Evans, J.C.; Lingeman, J.E., "A Novel Drug Eluting Ureteral Stent: A Prospective, Randomized, Multicenter Clinical Trial to Evaluate the Safety and Effectiveness of a Ketorolac Loaded Ureteral Stent", J. Urol., (2010), vol. 183, doi:doi:10.1016/j.juro.2009.11.035, pp. 1037-1043, XP026938397.

Lange, D.; Bidnur, S.; Hoag, N.; Chew, B.H., "Ureteral stent-associated complications[mdash]where we are and where we are going", NAT REV UROL, (2015), vol. 12, doi:doi:10.1038/nrurol.2014.340, pp. 17-25, XP055383632.

Lu, S.; Neoh, K.G.; Kang, E.-T.; Mahendran, R.; Chiong, E., "Mucoadhesive polyacrylamide nanogel as a potential hydrophobic drug carrier for intravesical bladder cancer therapy", Eur. J. Pharm. Sci., (2015), vol. 72, doi:doi:10.1016/j.ejps.2015.03.006, pp. 57-68, XP029124475.

Mendez-Probst, C.E.; Goneau, L.W.; Macdonald, K.W.; Nott, L.; Seney, S.; Elwood, C.N.; Lange, D.; Chew, B.H.; Denstedt, J.D.; CADI, "The use of triclosan eluting stents effectively reduces ureteral stent symptoms: a prospective randomized trial", BJU INT., (2012), vol. 110, doi:doi:10.1111/j.1464-410X.2011.10903.x, pp. 749-754, XP055370006.

Munoz, J.J .; Ellison, L.M., "Upper tract urothelial neoplasms: incidence and survival during the last 2 decades", J. UROL., (2000), vol. 164, doi:doi:10.1016/S0022-5347(05)67019-X, pp. 1523-1525, XP005553928.

Nunes, A. V; Rodriguez-Rojo, S.; Almeida, A.P.; Matias, A.A.; Rego, D.; Simplicio, A.L.; Bronze, M.R.; Cocero, M.J.; Duarte, C.M.M, "NCCN Clinical Practice Guidelines in Oncology (NCCN Guidelines®) Bladder Cancer", J. Control. Release, (2010), vol. 148, p. ELL-2.

Papadopoulos, E.; Yousef, G.; Scorilas, A., "Gemcitabine impacts differentially on bladder and kidney cancer cells: distinct modulations in the expression patterns of apoptosis-related microRNAs and BCL2 family genes", Tumor Biol., (2015), vol. 36, doi:doi:10.1007/s13277-014-2190-8, pp. 3197-3207, XP036218273.

Pu, Y.S.; Chen, J.; Huang, C.Y.; Guan, J.Y.; Lu, S.H.; Hour, T.C., "Cross-resistance and combined cytotoxic effects of paclitaxel and cisplatin in bladder cancer cells", J. UROL., (2001), vol. 165, doi:doi:10.1016/S0022-5347(05)66298-2, pp. 2082-2085, XP005544912.

Sebaugh, J.L., "Guidelines for accurate EC50/IC50 estimation", Pharm. Stat., (2011), vol. 10, doi:doi:10.1002/pst.426, pp. 128-134, XP055254257.

Shaikh, M.; Kichenadasse, G.; Choudhury, N.R.; Butler, R.; Garg, S., "Non-vascular drug eluting stents as localized controlled drug delivery platform: preclinical and clinical experience", J. Control. Release, (2013), vol. 172, doi:doi:10.1016/j.jconrel.2013.08.010, pp. 105-117, XP028772919.

Vandana, V.; Teja, A.S., "The solubility of paclitaxel in supercritical C02 and N20", Fluid Phase Equilib, (1997), vol. 135, pp. 83-87.

Yoda, S.; Sato, K.; Oyama, H.T., "Impregnation of paclitaxel into poly(dl-lactic acid) using high pressure mixture of ethanol and carbon dioxide", RSC ADV., (2011), vol. 1, pp. 156-162.

Yu, Q.; Zhang, J.; Zhang, G.; Gan, Z., "Synthesis and Functions of Well-defined Polymer-drug Conjugates as Efficient Nanocarriers for Intravesical Chemotherapy of Bladder Cancera", MACROMOL. BIOSCI., (2015), vol. 15, pp. 509-520.

Barros, A., "Biodegradable drug-eluting stents: Targeting urothelial tumors of upper utinary tract," Eur Urol Suppl, 2016, 15(3) 938.

Jang, S., "Stents with specialized functions: drug-eluting stents and stents with antireflux devices," Gastrointest Interv 2015, vol. 4. 50-54.

Yang, L., "Ureteral stent technology: Drug-eluting stents and stent coatings," Asian Journal of Urology (2015) vol. 2, p. 194-201.

\* cited by examiner

US 11,998,665 B2

BIODEGRADABLE URETERAL STENTS, METHODS AND USES THEREOF

CROSS-REFERENCE TO RELATED APPLICATIONS

This application is a U.S. National Stage Application under 35 U.S.C. § 371 of International Patent Application No. PCT/IB2017/051448, filed Mar. 13, 2017, which claims priority to Portugal Application No. 109229, filed Mar. 11, 2016, which are hereby incorporated by reference in their respective entireties.

TECHNICAL FIELD

The present disclosure relates to biodegradable ureteral stents comprising an anti-cancer drug, and to a composition for use in medicine that may be used to ensure patency of a channel, namely a mammal ureter, for example, an obstructed ureter by a urinary stone, neoplasia or by a surgical procedure.

BACKGROUND

Upper urinary tract urothelial carcinoma (UTUC) accounts for 5-10% of urothelial carcinomas and is a disease that has not been widely studied as carcinoma of the bladder. To avoid the problems of conventional therapies, such as the need for frequent drug instillation due to poor drug retention, we developed a biodegradable ureteral stent (BUS) impregnated by supercritical fluid $CO_2$ ($scCO_2$) with the most commonly used anti-cancer drugs, namely paclitaxel, epirubicin, doxorubicin, and gemcitabine. The release kinetics of anti-cancer therapeutics from drug-eluting stents was measured in artificial urine solution (AUS). The in vitro release showed a faster release in the first 72 h for the four anti-cancer drugs, after this time a plateau was achieved and finally the stent degraded after 9 days. Regarding the amount of impregnated drugs by $scCO_2$, gemcitabine showed the highest amount of loading (19.57 $\mu g_{drug}/mg_{polymer}$: 2% loaded), while the lowest amount was obtained for paclitaxel (0.067 $\mu g_{drug}/mg_{polymer}$: 0.01% loaded). A cancer cell line (T24) was exposed to graded concentrations (0.01 to 2000 ng/ml) of each drugs for 4 and 72 hours to determine the sensitivities of the cells to each drug ($IC_{50}$). The direct and indirect contact study of the anti-cancer biodegradable ureteral stents with the T24 and HUVEC cell lines confirmed the anti-tumoral effect of the BUS impregnated with the four anti-cancer drugs tested, reducing around 75% of the viability of the T24 cell line after 72 h and demonstrating minimal cytotoxic effect on HUVECs cells.

Upper tract urothelial carcinoma (UTUC) can be located in the lower (bladder and urethra) or upper (renal pelvis and ureter) urinary tract (Babjuk et al., 2013). UTUC are aggressive urologic cancers with propensity for multifocality, local recurrence, and metastasis (Audenet et al., 2013b). They are uncommon compared to bladder cancer, but 60% of UTUCs are invasive at diagnosis. Urothelial carcinomas (UCs) are the fourth most common type of tumors (Munoz and Ellison, 2000). The treatments available fall into two categories: a kidney-sparing surgery with the application of the adjuvant topical agents such as *bacillus* Calmette-Guerin (BCG) vaccine, mitomycin C or other anti-cancer drugs; and, in the majority of the cases, radical nephrectomy is performed, followed by chemotherapy. The UTUC are urothelial tumors, therefore drugs such paclitaxel, doxorubicin and gemcitabine are expected to have a similar therapeutic efficacy as in bladder cancer (Audenet et al., 2013b; Hellenthal et al., 2009). Some studies examined the role of chemotherapy for UTUC, and there appears to be an overall survival and disease-free survival benefit for anti-cancer drugs based adjuvant chemotherapy (Hellenthal et al., 2009).

Drugs like paclitaxel, mitomicin C, doxorubicin and gemcitabine have been reported in different studies as a drugs that can be incorporated in polymeric materials in order to obtain an intravesical drug delivery (IDD) system in urological tract (Hadaschik et al., 2008; Lu et al., 2015a; Papadopoulos et al., 2015). For intravesical chemotherapy, hydrophobic anti-cancer drugs offer a distinctive benefit of superior permeability through the urothelium as compared to hydrophilic drugs (Audenet et al., 2013a; Lu et al., 2015b). One innovative idea explored by Lifshitz et al. (MitoGel™) is the use of an hydrogel with mitomicin C which solidifies at body temperature and can provide prolonged retention of the therapeutic agent and a slow, sustained release (D. et al., 2014).

In this study we hypothesized a new concept for the delivery of these anti-cancer drugs using a drug-eluting biodegradable ureteral stent, combining hydrogel technology with conventional ureteral stents. Different drug-eluting ureteral stents have been used extensively in cardiovascular and different applications (Khan et al., 2012; Shaikh et al., 2013), but in urology it is still a new area (Lange et al., 2015). Some studies reported the impregnation of drugs like triclosan (Triumph®) (Mendez-Probst et al., 2012) and ketorolac (Lexington™) (Krambeck et al., 2010) in polyurethane based stents, with the objective to reduce bacterial adhesion, biofilm formation and encrustation to improve patient comfort by decreasing flank pain. These studies have demonstrated that in preclinical and clinical tests, drug-eluting conventional double-J ureteral stents have limited effectiveness possibly because of poor drug delivery to the ureteral tissues (Krambeck et al., 2010; Lange et al., 2015; Mendez-Probst et al., 2012).

These facts are disclosed in order to illustrate the technical problem addressed by the present disclosure.

General Description

The present disclosure relates to a biodegradable ureteral stents comprising an anti-cancer drug, and to a composition for use in medicine that may be used to ensure patency of a channel, namely a mammal ureter, for example, an obstructed ureter by a urinary stone, neoplasia or by a surgical procedure.

The biodegradable ureteral stents (BUS) disclosed in the present disclosure unexpectedly allow a proper release of anti-cancer drugs, thus extending the duration of the treatment and increasing the efficacy of the treatment and does not affect the proprieties of the biodegradable ureteral stents.

An aspect of the present disclosure relates to a biodegradable stent comprising a polymeric substrate wherein
 the polymeric substrate comprises 10-50% (w/w) of alginate
 45-85% (w/w) of gelatine;
 a polymeric biodegradable resin for coating said polymeric substrate;
 and no more than 10% (w/w) of an anti-cancer drug.

In an embodiment for better results, the biodegradable stent of the present disclosure may comprises no more than 5% (w/w) anti-cancer drug, preferably no more than 4.95% (w/w).

In an embodiment for better results, the biodegradable stent of the present disclosure may comprises at least one anti-cancer drug is selected from the list consisting of paclitaxel, epirubicin, doxorubicin, gemcitabine, and mixtures thereof.

In an embodiment for better results, the biodegradable stent of the present disclosure may comprises one of the following anti-cancer drug mixture: paclitaxel and epirubicin; or paclitaxel and doxorubicin; or paclitaxel and gemcitabine; or epirubicin and doxorubicin; or epirubicin and gemcitabine; or doxorubicin and gemcitabine; or paclitaxel, epirubicin and doxorubicina; or epirubicin, doxorubicina and gemcitabine; or paclitaxel, epirubicin and gemcitabine.

In an embodiment for better results, the polymeric substrate may comprises 20-40% (w/w) of alginate and 55-70% (w/w) of gelatine.

In an embodiment for better results, the resin may be added in a solution having a concentration of 3-50% (w/v), in particular 10-20% (w/v), more in particular 5-10% (w/v).

In an embodiment for better results, the biodegradable stent of the present disclosure may further comprises a contrast agent, namely an X-ray contrast agent.

In an embodiment for better results, the biodegradable stent of the present disclosure may comprises
  2-5% (w/w) of a contrast agent, namely bismuth (III) carbonate;
  a polymeric substrate comprising 20-40% (w/w) of alginate and 55-70% (w/w) of gelatine.

In an embodiment for better results, the biodegradable stent of the present disclosure may comprises 5% (w/w) of a contrast agent, namely bismuth (III) carbonate; a polymeric substrate comprising 30% (w/w) of alginate and 65% (w/w) of gelatine.

In an embodiment for better results, the resin may be selected from the following list: polycaprolactone resin, polyglycolide and its copolymers: poly(lactic-co-glycolic acid) with lactic acid, poly(glycolide-co-caprolactone) with ε-caprolactone, and poly (glycolide-co-trimethylene carbonate) with trimethylene carbonate, or mixtures thereof, in particular polycaprolactone.

In an embodiment for better results, the contrast agent is selected from the following list: barium salts, bismuth salts, spinel pigments, or mixtures thereof, in particular bismuth (III) carbonate.

In an embodiment for better results, the biodegradable stent of the present disclosure may further comprises a crosslinking agent. Preferably, wherein said crosslinking agent is selected from the following list: ionic crosslinking agents including monovalent or divalent ions, from which
  the cation is calcium, magnesium, barium, strontium, boron, beryllium, aluminium, iron, copper, cobalt, lead or silver;
  the anion being selected from the group consisting of chloride, nitrate, phosphate, citrate, borate, succinate, maleate or oxalate, or mixtures thereof; in particular calcium chloride.

In an embodiment for better results, the biodegradable stent of the present disclosure may further comprises a second anti-cancer drug selected from the following list: methotrexate, vinblastine, cisplatin, granulocyte colony-stimulating factor, carboplatin, 5-fluorouracil, ifosfamide, pemetrexed, mitomycin C, capecitabine, Bacillus Calmette-Guerin (BCG) or mixtures thereof.

In an embodiment for better results, the biodegradable stent of the present disclosure may further comprises an anti-inflammatory agent, an anti-microbial agent, an antiviral agent, or mixtures thereof.

In an embodiment for better results, the anti-cancer drug of the biodegradable stent may be impregnated in the stent, preferably by supercritical fluid $CO_2$.

In an embodiment for better results, the stent is a ureteral stent.

In another aspect of the present disclosure relates to a biodegradable stent may be use in regenerative medicine, tissue engineering, or in therapy, prophylaxy or treatment of cancer or urological diseases.

In another aspect of the present disclosure relates to a composition for use in medicine comprising alginate, gelatine, a polymeric biodegradable resin and no more than 10% (w/w) of an anti-cancer drug,
  wherein said composition is administrated in a biodegradable stent,
  wherein said stent comprises 10-50% (w/w) of alginate, 45-85% (w/w) of gelatine; a polymeric biodegradable resin for coating said polymeric substrate; and no more than 5% (w/w) anti-cancer drug.

In an embodiment for better results, the composition of the present disclosure may comprises 5% (w/w) of the anti-cancer drug, preferably no more than 4.95% (w/w) of the anti-cancer drug.

In an embodiment for better results, the composition of the present disclosure may comprises at least one anti-cancer drug is selected from the list consisting of paclitaxel, epirubicin, doxorubicin, gemcitabine, and mixtures thereof.

In an embodiment, the composition of the present disclosure may be use in regenerative medicine, tissue engineering, or in therapy, prophylaxy or treatment of cancer or urological diseases.

BRIEF DESCRIPTION OF THE DRAWINGS

The following figures provide preferred embodiments for illustrating the description and should not be seen as limiting the scope of invention.

DETAILED DESCRIPTION

Figure 1:
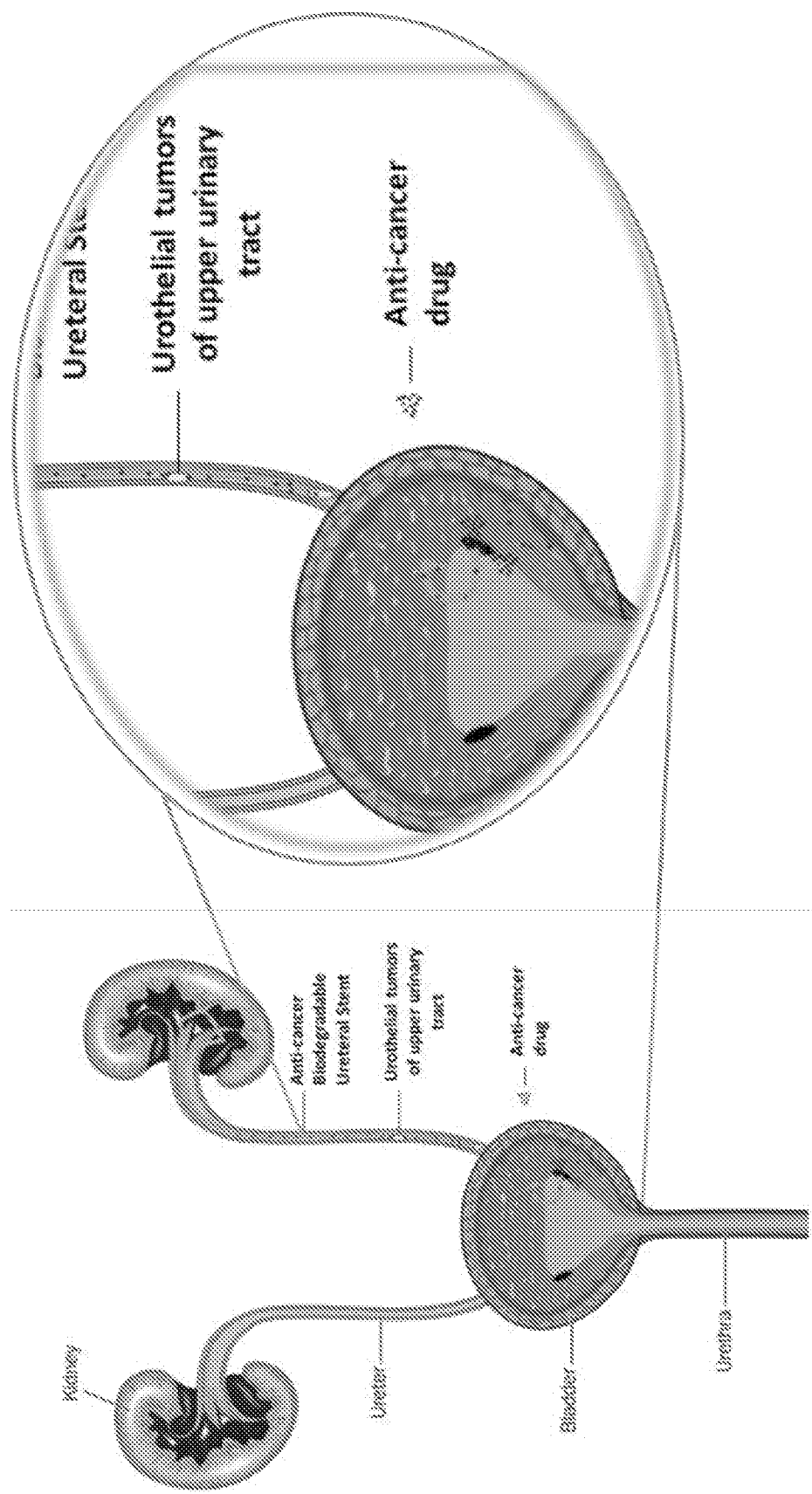
FIG. 1: Illustration of the concept of anti-cancer drug eluting biodegradable ureteral stent as a potential drug delivery system for UTUC therapy.

The present disclosure relates to a biodegradable ureteral stents comprising an anti-cancer drug, and to a composition for use in medicine that may be used to ensure patency of a channel, namely a mammal ureter, for example, an obstructed ureter by a urinary stone, neoplasia or by a surgical procedure.

In an embodiment, hydrophobic anti-cancer drugs, paclitaxel, doxorubicin, epirubicin, and/or gemcitabine, among others were impregnated by supercritical fluid technology in the biodegradable ureteral stent.

In an embodiment, alginic acid sodium salt, gelatin, calcium chloride, chlorophorm, ethanol and bismuth (III) carbonate basic were purchased from Sigma-Aldrich (Germany). Potassium dihydrogen ortho-phosphate (99.5%) and magnesium chloride hexahydrate (99%) were obtained from Riedel-de Haën (Germany). Polycaprolactone resin PCL 787, commercially available as TONE' polymer, was obtained from Union Carbide Chemicals and Plastics Division, Bound Brook, New Jersey. Artificial urine solution (AUS), paclitaxel 99.5% (PA), doxorubicin 98% (DOX), epirubicin 99% (EP), gemcitabine 99% (GEM) from Fisher Scientific (U.S.A.). Carbon dioxide (99.998 mol %) was supplied by Air Liquide (Portugal). All reagents were used as received without any further purification.

Briefly, polymers were dissolved in hot distilled water (70° C.). The solution was stirred for 1 hour and the polymeric solution was injected in a mold to obtain a tubular structure. After 1 hour the piece was taken out of the mold and placed in an alcohol solution (100% ethanol) for 1 hour. BUS were then transferred into a crosslinking solution of calcium chloride ($CaCl_2$)), preferably 0.48M, at room temperature. After crosslinking, BUS were relocated in an alcoholic solution (100% ethanol) to obtain an alcohol gel. The biostent of the present subject-matter were dried using a high-pressure vessel with supercritical carbon dioxide (scCO2) at 40° C. and 100 bar for 90 min, in continuous mode. The coating of the stents was performed by immersion in a 10% of polycaprolactone (PCL) resin 787, preferably (Mw 80,000 g mol-1) dissolved in chloroform.

In an embodiment, a supercritical $CO_2$ impregnation of anti-cancer drugs was performed, in the biodegradable ureteral stents (BUS) of the present disclosure. The were biodegradable ureteral stents prepared were placed in high-pressure vessel with anti-cancer drugs (10 mg) according to FIG. 2. The anti-cancer drugs were impregnated in the stents with and without the presence of a co-solvent. The $scCO_2$ impregnation conditions used were 100 bar at 40° C. and 90 min. Carbon dioxide was liquefied and pumped to the desired pressure using a membrane pump (MCPV-71, Haskel, Germany). Impregnation took place in batch mode for 90 min followed by fast depressurization of the system. When a co-solvent was employed, 10% (v/v) ethanol was used. A commercial non-degradable ureteral stent (Biosoft® duo, Porges, Coloplast) was impregnated with same drugs at the same conditions with co-solvent, to be used as a control. To enhance the mechanical properties of the stent a PCL coating was applied. To evaluate the effect of coating on the release of the drugs the condition BUS+Co-Solvent was prepared twice and one of this batches was coated with PCL resin. The nomenclature used for each condition is presented in table 1.

TABLE 1

Nomenclature of each condition study of anti-cancer drugs impregnated by supercritical fluid process.

| | BUS | BUS + Co-Solvent* | (BUS + Co-Solvent) + PCL Coating | Commercial stent |
|---|---|---|---|---|
| Paclitaxel (PA) | $PA_{bio}$ | $PA_{EtOH}$ | PAcoat | $PA_{Com}$ |
| Epirubicin (EP) | $EP_{bio}$ | $EP_{EtOH}$ | EPcoat | $EP_{Com}$ |
| Doxorubicin (DOX) | $DOX_{bio}$ | $DOX_{EtOH}$ | DOXcoat | $DOX_{Com}$ |
| Gemcitabine (GEM) | $GEM_{bio}$ | $GEM_{EtOH}$ | GEMcoat | $GEM_{Com}$ |

In an embodiment, after impregnation a batch of BioStents were coated with PCL resin, and a new condition (Drug.COAT) was evaluated.

The anticancer drugs impregnation yield (I) was calculated from Eq. (1):

$$I(\%) = m_{drug}/m_{stent} + m_{drug} \times 100 \quad \text{Eq. (1)}$$

where $m_{stent}$ is the polymer mass at the beginning of the process and the $m_{drug}$ is the mass of the respective anticancer drug released after complete degradation of the stents in AUS. Anti-cancer drugs concentration was calculated from a calibration curve prepared from standard solutions. The samples were analyzed by UV-spectroscopy using a microplate reader (SpectraMax i3, Molecular Devices, USA) at the maximum absorbance for each drug (227 nm for PA, 254 nm for EP and DOX and 268 nm for GEM). All the experiments were performed in triplicate.

In an embodiment, the determination of anti-cancer drugs release from biodegradable ureteral stents were perform, the release kinetics of developed anti-cancer drug-eluting biodegradable ureteral stents was measured in artificial urine solution (AUS). The in vitro anti-cancer drugs, in particular paclitaxel, epirubicin, doxorubicin and gemcitabine release from the impregnated biodegradable ureteral stents was performed in triplicate. 10 mg of impregnated sample were weighted and immersed in 10 ml of AUS at 37° C. with 60 rpm stirring. At predetermined time periods (0 min, 5 min, 15 min, 30 min, 1 h, 3 h, 5 h, 7.5 h, 24 h, 48 h, 72 h, 6 days and 10 days), an aliquot of 0.5 ml of the release solution was taken and the volume replaced with fresh AUS. Anti-cancer drugs concentration was calculated from a calibration curve prepared from standard solutions. Preferably The concentration of drug was determined by UV-spectroscopy as described above. In particular, The samples were analyzed by UV-spectroscopy using a microplate reader (Synergy HT, Bio-Tek Instruments, USA) at the maximum absorbance for each drug which was 227 nm for PA, 254 nm for EP and DOX and 268 nm for GEM.

In an embodiment, the present disclosure used a human urothelial carcinoma cell line, T24 (ATCC, U.S.A.) as a cancer cell line to model the urothelial carcinoma and human umbilical vein endothelial cells, HUVEC, (ATCC, U.S.A.) as a control, non-cancerous cell line. The T24 cell line and HUVEC cells were cultured in RPMI-1640 and EGM™-2 medium, respectively, with (10% fetal bovine serum (FBS), 1 mM L-glutamine and 1% penicillin/streptomyocin), Cells were maintained at 37° C. in a humidified 5% CO2 atmosphere.

In an embodiment, in vitro efficacy of anti-cancer drugs against T24 cells and HUVEC cells-$IC_{50}$ determination. The cytotoxicity of paclitaxel, epirubicin, doxorubicin and gemcitabine was evaluated by determining the viability of T24 and HUVEC cells after exposure to medium containing the free drug at a range of concentrations from 0.01 to 2000 ng/ml. Free drugs in medium were prepared by first dissolving the anticancer drugs in DMSO (50 mg/ml) and this solution was then diluted in culture medium to achieve the desired concentration. A standard MTT cell proliferation assay (CellTiter 96® Aqueous One Solution Cell Proliferation Assay) was used to test cell viability and was performed on both cell lines to determine the half maximal inhibitory concentration (1050) of each drug. 5000 cells per well were seeded in a 96-well plate with 100 μl medium for T24 and HUVEC cells. After incubation for 24 h, the medium in each well was aspirated off and the cells were exposed to 100 μl of fresh medium containing the drugs at various concentrations for 4 h and 72 h. The cells after 4 h treatment were further cultured for 72 h in fresh (drug-free) medium. After that, the culture medium in each well was replaced by 100 μl of medium and 20 μl of CellTiter 96® AQueous One Solution Reagent, followed by 4 h incubation at 37° C. A latex rubber extract was used as negative control for cell death; while cell culture medium was used as positive control. Cell viability was quantified by UV-spectroscopy, reading the formazan absorbance at 490 nm in a microplate reader (SpectraMax i3, Molecular Devices, USA). Each sample formulation and control was tested using 12 replicates.

In an embodiment, the 1050 was determined from the fitting of the curve of cell viability, measured by MTT and the drug concentration. The fitting was performed using GraphPad software (GraphPad Prism 6.00 software, San Diego, USA).

The in vitro anti-tumoral/cancer effect of anti-cancer drug-eluting biodegradable ureteral stents by indirect and direct contact with T24 cells and HUVECs (Human Umbilical Vein Endothelial Cells, was evaluated.

In an embodiment, the anti-cancer effect of the anti-cancer drug-eluting biodegradable ureteral stents in human urothelial carcinoma cell line was evaluated by determining the viability of T24 cells by indirect and direct contact. HUVEC was used as non-cancerous, control cell line. The T24 cell line and HUVEC cells were cultured in RPMI-1640 and EGM™-2 medium, respectively with (10% fetal bovine serum (FBS), 1 mM L-glutamine and 1% penicillin/streptomyocin). By indirect contact, the effect of the released drug as well as leachables from the biodegradable ureteral stents were evaluated, placing the stents in fresh medium after 4 h and 72 h. On the other hand, by direct contact 10 mg of stent was placed directly in contact with a cell layer in each well. Both tests were performed for 4 h and 72 h. The viability of the cells was performed using a standard MTT test. Briefly, 5000 cells per well were seeded in a 96-well plate with 100 μL medium for T24 and HUVEC cells. After incubation for 24 h, the medium in each well was aspirated and the cells exposed to medium containing the extracts of the stents in the indirect contact study. In the direct contact the cells were exposed to 100 μL of fresh medium in the presence of the stent. The cells after 4 h treatment were further cultured for 72 h in fresh medium. After that, the culture medium in each well was replaced by 100 μL of medium and 20 μL of CellTiter 96® AQueous One Solution Reagent, followed by 4 h incubation at 37° C. Cell culture medium and the non-impregnated stents (BUS and commercial stent) were used as negative controls. Each sample formulation and control was tested with 3 replicates.

In an embodiment, light microscopy was performed. Cells cultured on the bottom of the well plate, after 4 and 72 h direct contact were observed by under light microscope (Axio Imager Z1m, Zeiss, Germany) in order to visually assess the effect on evaluate their morphology. Images were taken with a magnification of 10× of T24 cells after 4 h and 72 h of exposure by direct contact to biodegradable ureteral stents impregnated with the anti-cancer drugs. Control experiments were carried out in T24 cells and drug-free stents for 72 h.

In an embodiment, all data values are presented as mean±standard deviation (SD). Statistical analysis was performed using Graph Pad Prism 6.00 software (San Diego, USA). Statistical significances (The normality of the data distribution for each sample was evaluated using the Shapiro-Wilk test (confirmed in all the cases for $p<0.05$). Significant differences between samples were evaluated using the t-test (*$p<0.05$, $p<0.01$ and *$p<0.001$) were determined using one-way analysis of variance (ANOVA) for an average of three to twelve replicates, followed by post hoc Tukey's test for all pair-wise mean comparisons.

Figure 2:
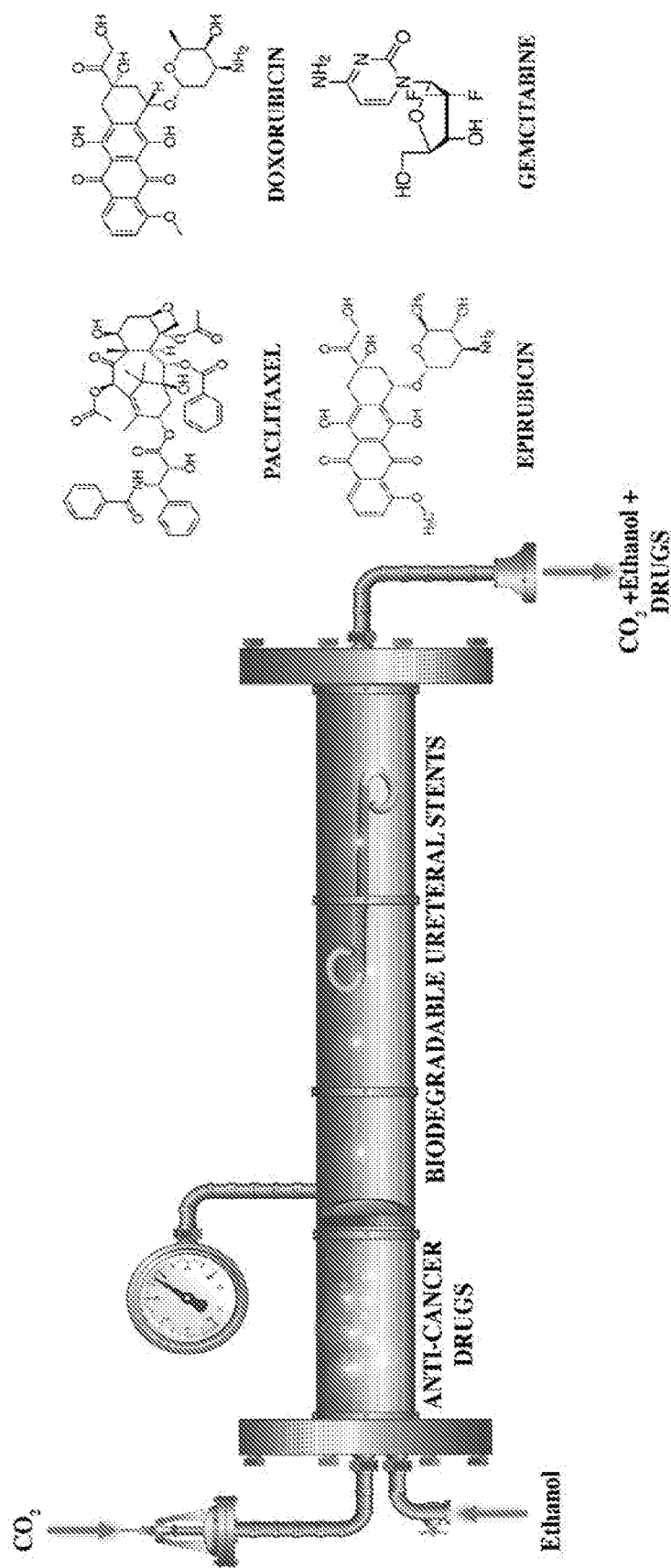
FIG. 2: Illustration of the supercritical fluid process impregnation and apparatus of the anti-cancer drugs used in biodegradable ureteral stent.
Figure 3:
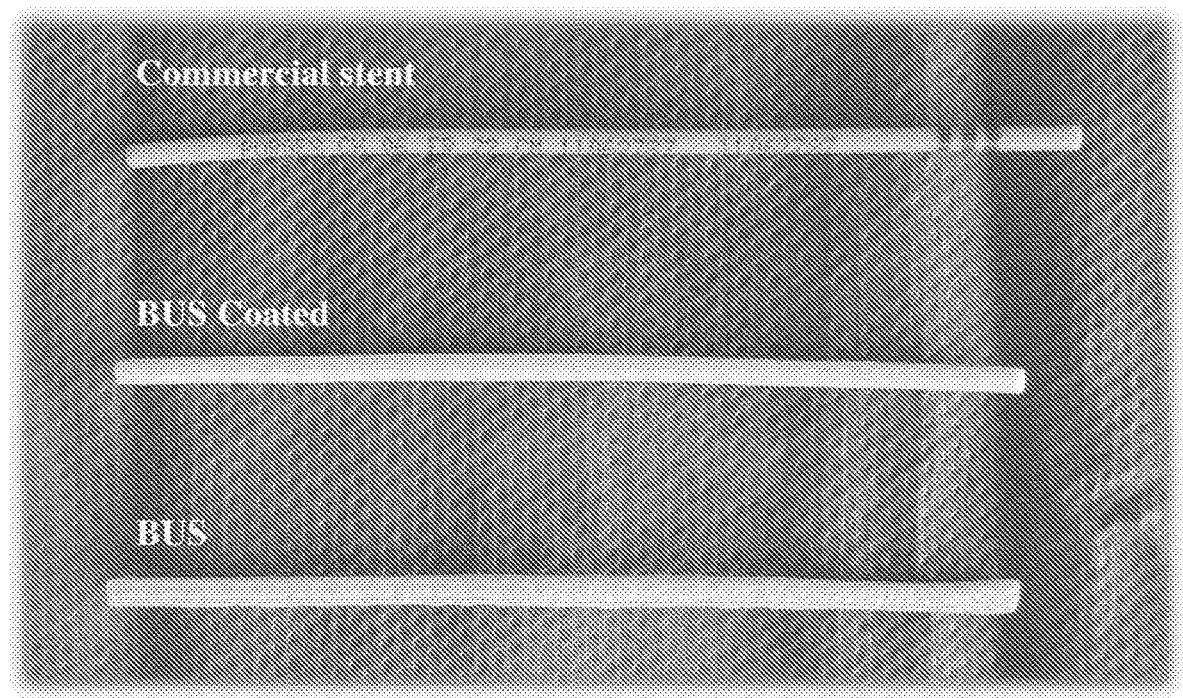
FIG. 3: Illustration of a section of commercial non-degradable ureteral stent (Biosoft® duo, Porges, Coloplast) BUS coated with PCL resin and BUS stents prepared after impregnation.

In an embodiment, the biodegradable ureteral stents from natural origin polymers were prepared as previously described (FIG. 3), and the anticancer drugs were loaded in BUS by scCO2, as illustrated in FIG. 2. scCO2 offers advantages over other impregnation solvents as it is an environmentally friendly, non-flammable, and non-toxic solvent, highly abundant and low cost. Furthermore, at the end of the impregnation process, and after the depressurization step, the final product is obtained in a dry form avoiding the need for subsequent drying and purification steps. Furthermore, the solvent can be recycled and reused. (Champeau et al., 2015).

According to Kazarian et al. (Kazarian and Martirosyan, 2002; Kazarian, 2000) there are mostly two mechanisms which describe impregnation by supercritical fluids. One is the simple deposition of the drugs in the swollen matrix when the system is depressurized. In this mechanism, the drug is solubilized in CO2 and is placed in contact with the polymeric matrix for a predetermined time. After this procedure, and upon depressurization, the CO2 molecules rapidly leave the polymer matrix, the solubilized drug precipitates and is deposited within the polymeric network. This mechanism is highly dependent on the swelling ability of the polymeric matrix when in contact of the supercritical fluid. On the other hand, a second mechanism of impregnation described by Kazarian et al., is said to be more dependent on the affinity of the drug towards the polymeric matrix.

In an embodiment, the conditions used for the impregnation of anti-cancer drugs were the same as used for the drying of the stents (100 bar at 40° C. and 90 min) with and without the presence of a co-solvent. The addition of polar solvents to $scCO_2$ such as ethanol is known to increase the solubility of many polar substances, like the drugs used in this study, which have a large molecular weight and/or molecular polarity and hence low solubility in carbon dioxide (Yoda et al., 2011). The use of 10% ethanol was determined by the solubility of drugs in supercritical $CO_2$ reported in literature (JIAO et al., 2011; Suleiman et al., 2005; Vandana and Teja, 1997; Yoda et al., 2011).

In an embodiment, impregnation efficiency of anti-cancer drugs in the biodegradable ureteral stents (BUS) was determined as a function of mass (μg) of anti-cancer drugs per mass (mg) of the polymer. The results are presented in Table 2. In the DrugEtOH conditions, the amount of anti-cancer drug impregnated in the stents is higher, as it would be expected due to the co-solvent effect of ethanol in the enhancement of drug the solubility in CO2. The amount of impregnated paclitaxel in pure scCO2 (PAbio) was 0.046 μg mg-1, whereas those in PAEtOH condition was 30% higher (0.067 μg mg-1). A similar percentage was reported by Yoda et al. (Yoda et al., 2011) in which the authors report the impregnation of paclitaxel in an amorphous poly(DL-lactic acid) (PDLLA) matrix. The amount of paclitaxel impregnated by Yoda et al. in PDLLA was 2-3 times higher compared with the alginate/gelatin matrix obtained in this work. This can be justified by the higher affinity of the drug-CO2 solution in the hydrophobic PDLLA matrix (Kazarian, 2000). Furthermore, PDLLA may also have greater swelling in the presence of scCO2 than the alginate/gelatin polymer blend (Cooper, 2000; Yoda et al., 2011). Regarding the other drugs, the results show a 15% increase in the impregnation yield for EP, 12% for DOX and 8% for GEM when ethanol was used as a co-solvent. In the case of the Biosoft® duo, Porges, Coloplast stents the amount of drug impregnated is 6-times lower compared with BUS impregnated with paclitaxel under the same conditions. The lower amount of drug impregnated can be related with lower swelling ability of the polymeric matrix of the commercial stent in scCO2 and/or by lower affinity of the drugs with composition material of the Biosoft® duo, Porges, Coloplast stent.

AUS the PCL coating detaches from the surface, hence no significant differences between the release profile of the different drugs from the coated or uncoated stents are observed. In the case of the Commercial stent all drugs impregnated are released in the first 24 h. For the biodegradable system, it is noticeable that in the first 4 h a release of nearly 50% of the amount drug impregnated and the remaining drug was sustainably released until 72 h in AUS. The stent degraded after 9 days.

Figure 4:
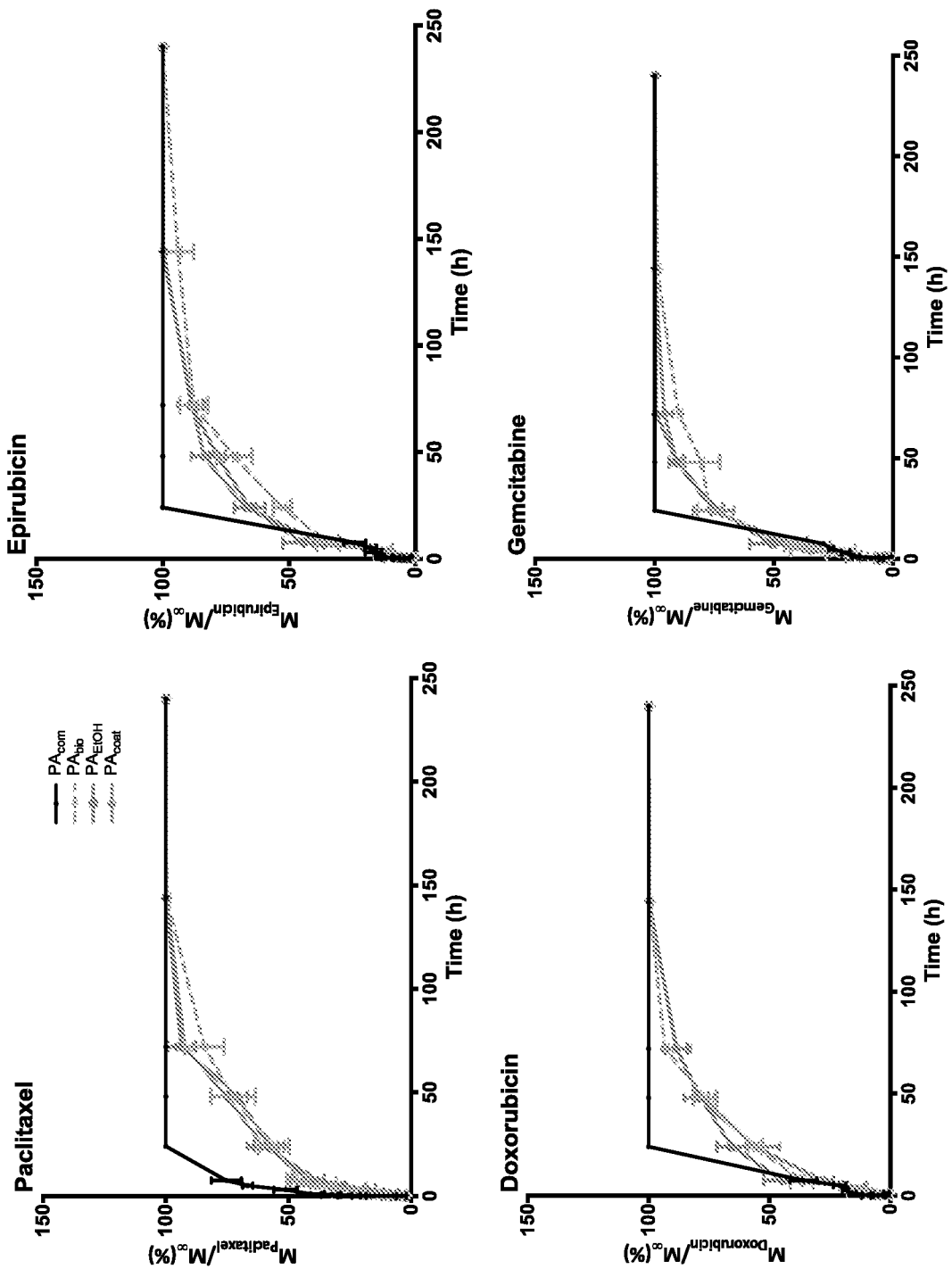
FIG. 4: Illustration of the cumulative anti-cancer drugs release from biodegradable and non-biodegradable ureteral stents in Artificial Urine Solution AUS (pH 5.5) at 37° C., for different conditions tested. The stent degraded after 9 days.

In an embodiment, in the non-degradable stent, we observed a faster release when compared with the BUS. This faster release may be justified due the poor impregnation on the synthetic polymer. In this case due to the highly dense polymer network the drugs did not penetrate deeply into the bulk of the polymeric matrix, but rather are located on or close to the surface of the stents and hence are more easily released to the medium (Lu et al., 2015b). In the case of the biodegradable stent, it is composed of 94% water with a highly porous polymer network. Furthermore, the acidic and high ionic strength of AUS may swell the stent facilitating the release. The release profile of these four anti-cancer drugs shown in FIG. 4 is promising for intravesical chemotherapy in UTUCs (Lu et al., 2015a).

Figure 5A:
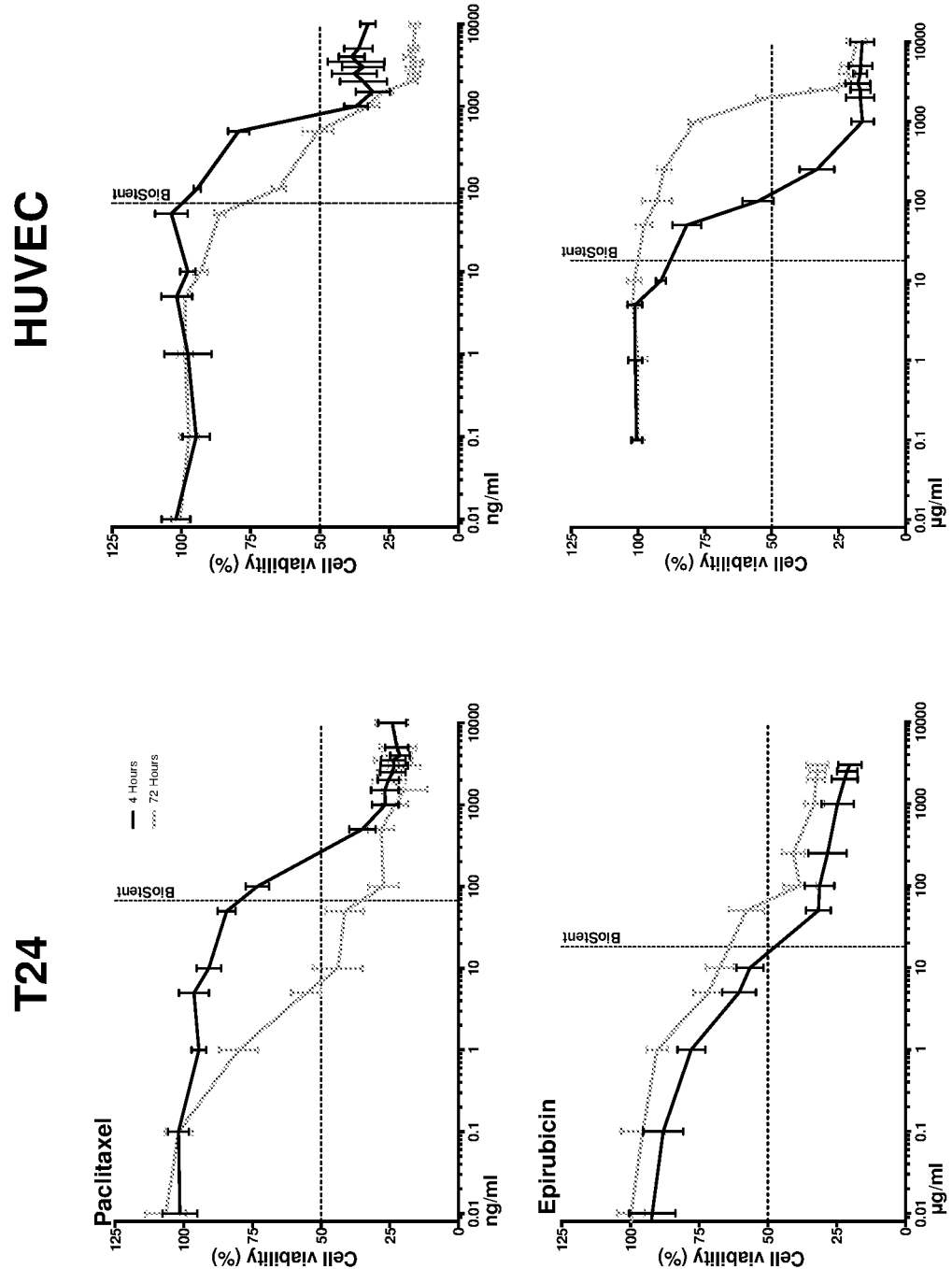
FIGS. 5A and 5B: Illustration of In vitro viability of T24 cells and HUVEC cells after exposure to the anti-cancer drugs at different concentrations for 4 h or 72 h. Cell viability is expressed as % of control. Vertical line represents the amount of drug impregnated by scCO2 in BioStent. Data shown is the average of at least 3 independent experiments.
Figure 5B:
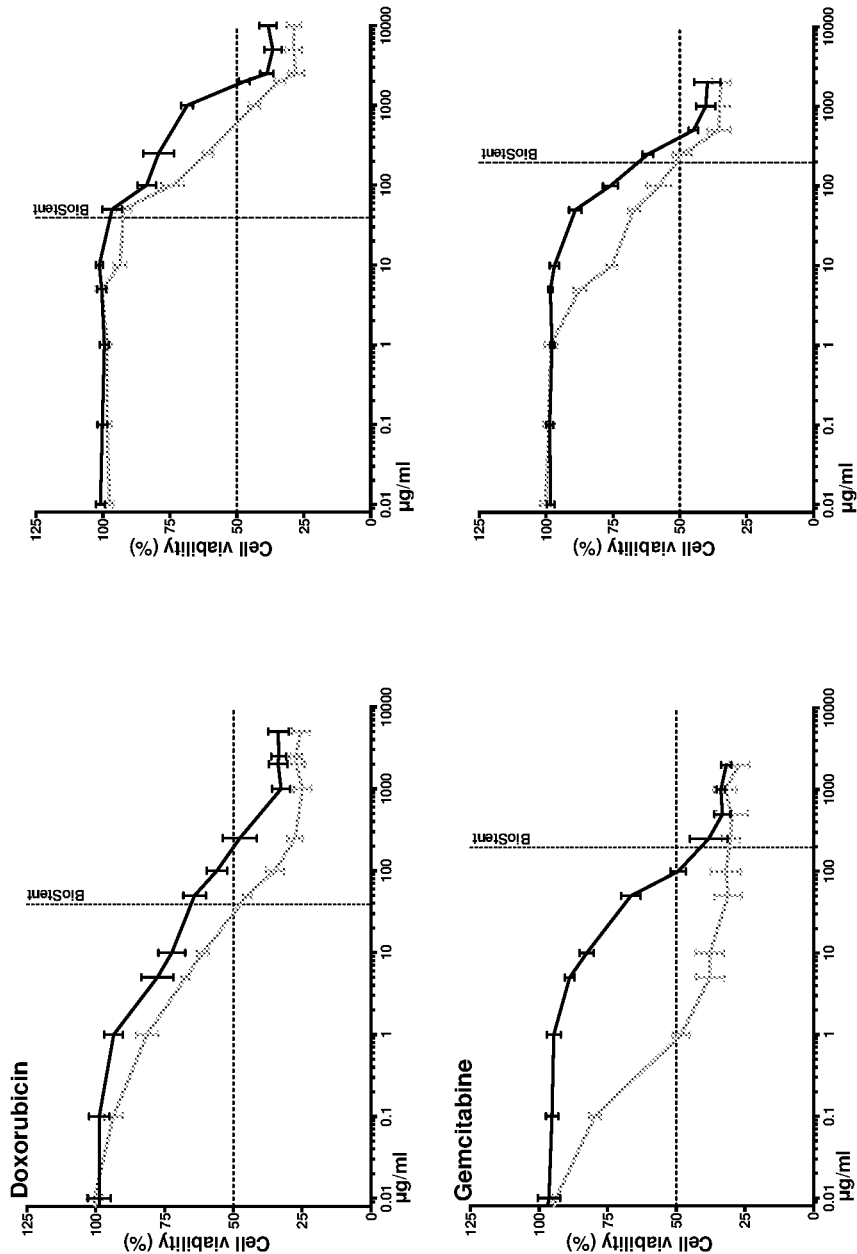

In an embodiment, the effect of the anti-cancer drugs (IC50) when in contact with T24 and HUVEC cells was investigated by a cell viability test, namely the MTT assay. From this, the $IC_{50}$ was calculated for each of the four drugs in each of the two cell lines. In this case, $IC_{50}$ is a measure of the concentration needed to inhibit cell survival, and is routinely used to specify the in vitro potency of a drug (Sebaugh, 2011). The T24 cell line was chosen as a muscle invasive urothelial cancer and the HUVEC cells were used as non-cancerous control cells. The cytotoxicity evaluation was carried out either after 4 h or 72 h of exposure of the cells to the free drugs at different concentrations (FIGS. 5 A and B). The four anti-cancer drugs showed to have a concentration-dependent inhibition profile of the survival of both the cancer cell line and HUVEC cells. In FIGS. 5 (A and B) it is possible to see, for both cell types the trend of

TABLE 2

Quantity of drug impregnated by scCO2 (operating conditions 90 min, 100 bar and 40° C.) ($\mu g_{drug}/mg_{polymer}$).

| | Paclitaxel | ±STD | Epirubicin | ±STD | Doxorubicin | ±STD | Gemcitabine | ±STD |
|---|---|---|---|---|---|---|---|---|
| $Drug_{bio}$ | 0.046 | 0.001 | 1.498 | 0.070 | 3.297 | 0.153 | 18.183 | 0.769 |
| $Drug_{ETOH}$ | 0.067 | 0.001 | 1.779 | 0.032 | 3.748 | 0.202 | 19.572 | 0.353 |
| $Drug_{Com}$ | 0.014 | 0.001 | 0.118 | 0.022 | 0.208 | 0.057 | 2.312 | 0.131 |

In an embodiment, in vitro release kinetics in artificial urine solution were perform. The release of anti-cancer drugs from the impregnated BioStent and commercial ureteral stents was performed in AUS at 37° C. in order to mimic the conditions in vivo. Artificial Urine solution (pH 5.5) was chosen as the release medium and this medium was regularly replaced to provide sink conditions. FIG. 4 shows the release profile of the drugs from the stents.

In an embodiment, similar release for the four anticancer drugs impregnated in the BUS was observed. Comparing the condition where the BUS is coated (Drugcoat) with the non-coated conditions, it is possible to conclude that the PCL coating of the BUS did not affect the release of the drugs in AUS. The PCL layer is delaminated from the surface of the stent due to the poor interfacial adhesion between the hydrophilic polymers gelatin+alginate and the hydrophobic PCL. Upon immersion in the physiological concentration-dependent cytotoxicity. These are similar, in all cases and as it would be expected the 72 h exposure present a higher killing efficacy. Comparing the results between the two cells it is possible to conclude that the cancer cells are much more sensitive to the anti-cancer drugs compared with the HUVEC cells.

In FIGS. 5 (A and B), a vertical line is plotted which corresponds to the amount of drug impregnated in BUS for each drug. The results show for all drugs that the amount of drugs impregnated in BUS is higher than $IC_{50}$ value of T24 cells and lower than $IC_{50}$ value of HUVEC cells. Importantly, this shows that the BUS impregnated in this study may have a cytotoxic effect against T24 cells but no effect against HUVEC cells. In the case of gemcitabine, the amount of drugs in BUS is still lower than the $IC_{50}$ of HUVECs but the amount of drug in theory has the ability to affect the HUVEC cells, reducing the cell viability near to 50% during the 72 h. In the case of direct contact method no effect on HUVECs was observed, Browne et al, suggested that delayed release can reduce the toxicity (Browne et al., 2012).

Figure 6:
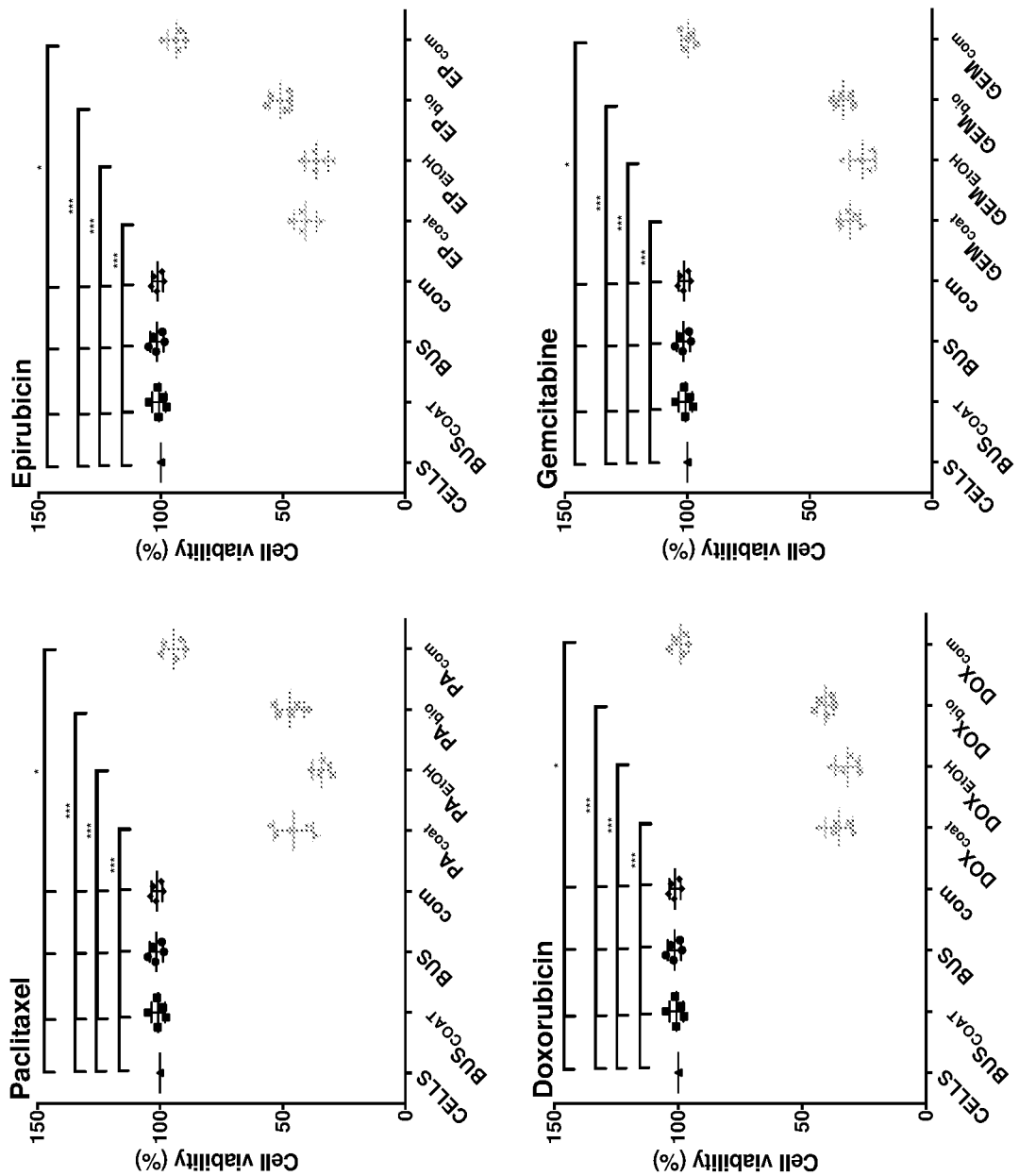
FIG. 6: Illustration of cell viability of T24 cancer cell line after 72 h exposure by indirect contact. Statistical significant differences were considered as *$p<0.05$, $p<0.01$ and *$p<0.001$.

In an embodiment, the four drugs have shown different cytotoxicity concentrations for the T24 and HUVEC cells. The results show to have time- and concentration-dependent cytotoxicity of T24 and HUVEC against the anti-cancer drugs tested. The $IC_{50}$ values are presented in Table 3. For T24, $IC_{50}$ at 4 h exposure time for paclitaxel is 281.98 ng/ml which is ~3 times lower than the corresponding value for HUVEC (849.81 ng/ml). When the exposure time is increased to 72 h the difference between the two [cells are even higher 7.30 ng/ml for T24 and 501.50 ng/ml to HUVEC cells. For the other drugs, the cells seem to be less sensitive. In these cases, the $IC_{50}$ values are in the range of µg/ml and not ng/ml as observed in paclitaxel profile. Comparing with the literature, the value obtained for paclitaxel after 72 h (7.30 ng ml$^{-1}$) is higher than with the $IC_{50}$ value obtained by Hadaschik et al. (2.85 ng ml$^{-1}$) (Hadaschik et al., 2008). Lu et al. (Lu et al., 2015a) and Yu et al. (Yu et al., 2015) report the $IC_{50}$ of doxorubicin for T24 cancer cells and the results have also shown to be concentration-dependent cytotoxicity, but presenting a different range of $IC_{50}$ values, 11.6 ng ml$^{-1}$ and 4 µg ml$^{-1}$, respectively. In the case of the gemcitabine, Papadopoulos et al. (Papadopoulos et al., 2015)

cancer cells and as a control HUVEC were also used. FIG. 6 shows the cytotoxicity assay of T24 cancer cell line and HUVEC cells after 72 h exposure by direct contact. A similar result to what was observed by indirect contact for T24 cancer cells, comparing the different conditions tested with killing efficacy of the impregnated stents. Nonetheless, all the conditions present a higher killing efficacy increasing around 10% in comparison with the indirect contact results. DrugEtOH conditions have once again shown have the highest anti-cancer effect, due to the higher amount of drug impregnated. The HUVEC cells, used as control cells, did not show compromised viability after incubation for 72 h in any of the conditions tested. Looking back to FIGS. 5 (A and B) it was expected see a cytotoxic effect particularly in the conditions with gemcitabine in contact with HUVEC cells, due to the close concentration of drug impregnated in the stent with the IC50 value determined, but this was not observed and the cell viability remained nearly 100%. Thus, the amount of anti-cancer drug impregnated in biodegradable ureteral stents by scCO2 had a killing efficacy of 75% in T24 cancer cells, but this did not affect the non-cancer cells (HUVEC).

In an embodiment, in the treatment of UTUC there is still no standard chemotherapy defined. The doses used for e.g in bladder cancer are in the order of 50 mg m−2 for paclitaxel, 30 mg m−2 for doxorubicin and epirubicin, and 75 mg m−2 for gemcitabine during the first 1-3 days (NCCN, n.d.). It is

TABLE 3

IC50 of the anti-cancer drugs at 4 h and 74 h for the T24 and HUVEC cells (±STD)

| | $IC_{50}$ | Paclitaxel (ng/ml) | Epirubicin (µg/ml) | Doxorubicin (µg/ml) | Gemcitabine (µg/ml) |
|---|---|---|---|---|---|
| T24 | 4 h | 281.98 ± 3.06 | 67.02 ± 2.34 | 187.07 ± 5.18 | 98.97 ± 1.29 |
| | 72 h | 7.30 ± 0.88 | 15.74 ± 1.02 | 29.28 ± 10.01 | 0.89 ± 0.27 |
| HUVEC | 4 h | 849.81 ± 6.48 | 2051.08 ± 33.21 | 2149.32 ± 58.21 | 413.57 ± 2.68 |
| | 72 h | 501.50 ± 7.67 | 139.11 ± 13.64 | 646.60 ± 21.35 | 237.24 ± 16.73 |

In an embodiment, the anti-tumoral/anti-cancer effect of the anti-cancer biodegradable ureteral stents developed was evaluated by determining the viability of both T24 cells and HUVEC by indirect and direct contact of the stents with cells. FIG. 6 presents the results for four drugs tested by indirect contact against T24 cancer cell after 72 h of exposure. The controls used were the T24 cells in a drug-free medium and the stents without drugs impregnated. The T24 cancer cells display similar behavior when in contact with drug-loaded stents as to when exposed to the different drugs tested. After 4 h and 72 h in contact with drug-released-medium the viability of cancer cells decreases in most cases around 25% and 50%, respectively. The condition when ethanol was used as a co-solvent (DrugEtOH), and thus had more drug impregnated in the stent, also presents a higher killing efficacy, around 65% for all drugs after 72 h of exposure. Considering the effect of the coating of the BUS (DrugCOAT) these present a slightly lower efficacy when compared with the non-coated stents. On the other hand, the commercial stent (DrugCom) shows a significantly lower killing efficacy (~10%) which may be due the lower amount of drug impregnated in the stent as observed in the impregnation results.

The surprisingly results obtained and the new concept of using ureteral stents with anti-cancer drugs for the treatment of carcinomas in the ureter justify the evaluation of the cancer cells viability in a closer way. The impregnated stents were placed in direct contact for 4 h and 72 h with the T24 hence, difficult to establish a comparison between the concentrations determined here (table 2) and the values reported. Nonetheless, the in vitro results presented here indicate that the systems developed have a significant potential in the delivery of such drugs in the upper urinary track, with a demonstrated in vitro efficacy. To increase the killing efficacy of the BUS more than one drug could be impregnated into the polymer matrix (Browne and Pandit, 2014), as different studies have demonstrated the higher cytotoxic and synergistic effect of combining more than one drugs administrated such as cisplatin with paclitaxel (Hadaschik et al., 2008; Pu et al., 2001).

Figure 7:
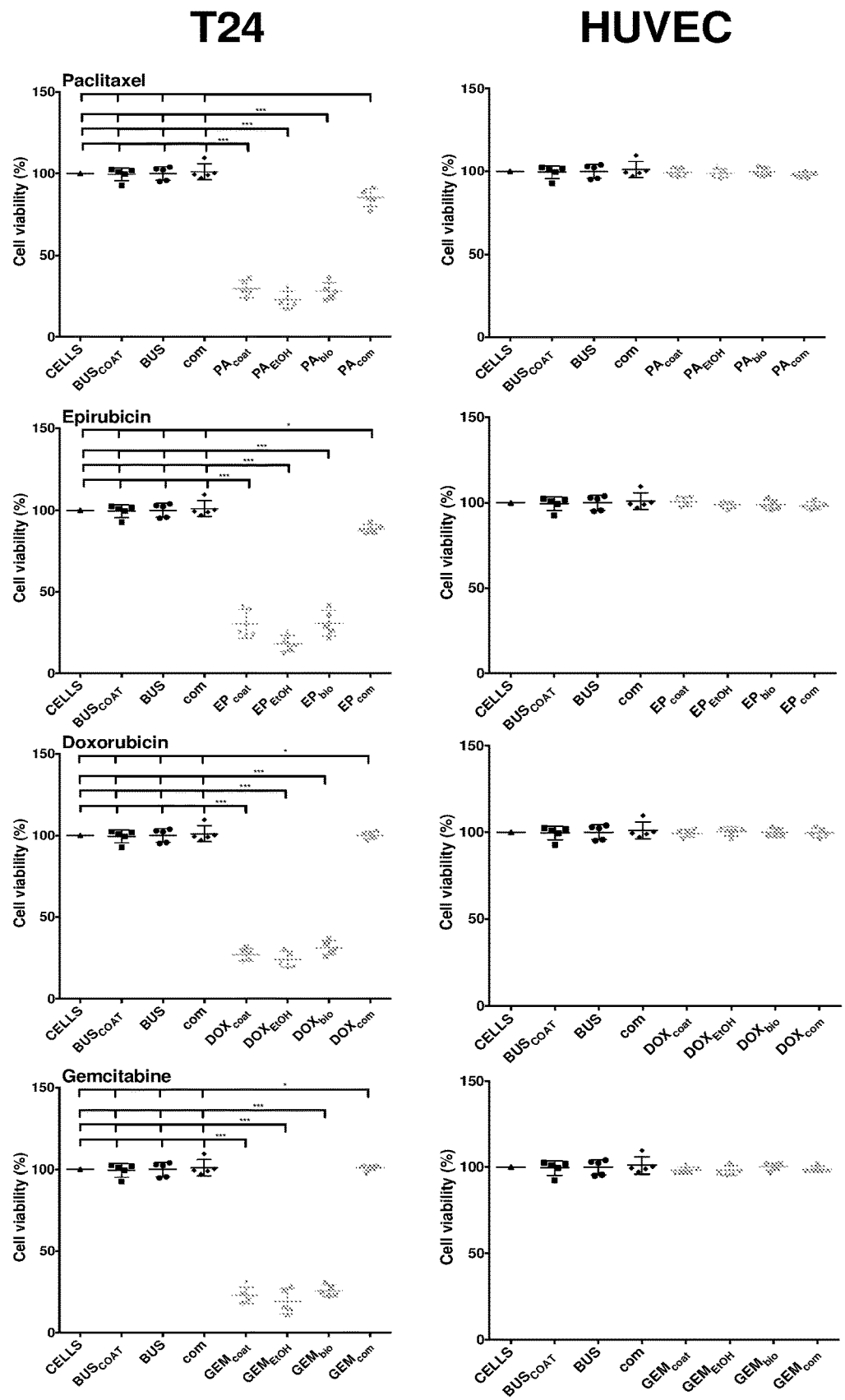
FIG. 7: Illustration of cell viability of T24 cancer cell line and HUVEC cells after 72 h exposure by direct contact. BUScoat is the BUS with the PCL coating without anti-cancer drugs impregnated. Statistical significant differences were considered as *$p<0.05$, $p<0.01$ and *$p<0.001$.
Figure 8:
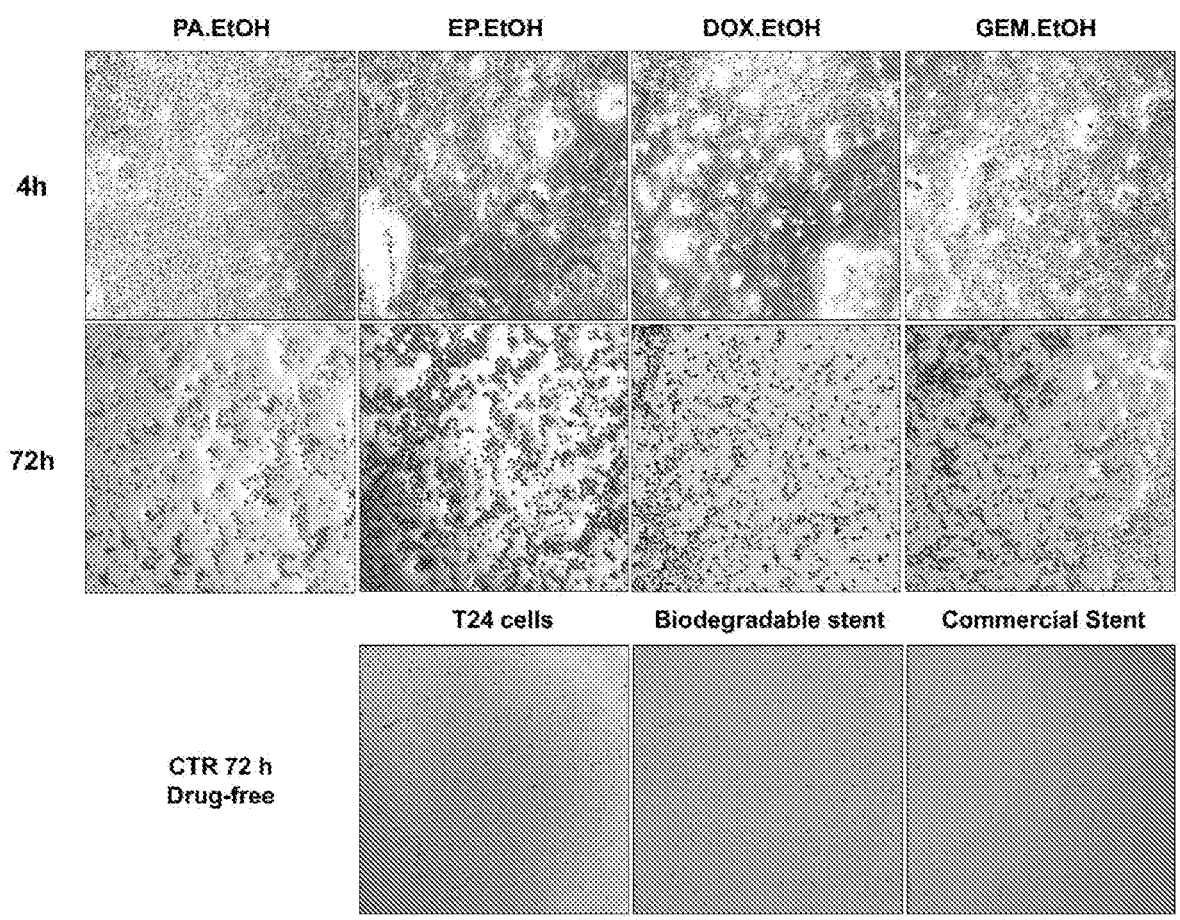
FIG. 8: Illustration of light microscopy images (10×) of T24 cells morphology after 4 h and 72 h of exposure by direct contact to biodegradable ureteral stents impregnated with the anti-cancer drugs. Control experiments were carried out in T24 cells and drug-free stents for 72 h.

In an embodiment, the effect of the biodegradable ureteral stents impregnated with the different anti-cancer drugs in the T24 cancer cells was investigated by light microscopy. FIG. 7 shows the light microscopy images of T24 cancer cells in contact with the BioStent impregnated with each of the four different anti-cancer drugs tested after 4 h and 72 h of direct contact. After 4 h exposure time it is possible to see that majority of the T24 cells are confluent with polygonal cells [40] with some cells starting to present a rounded shape indicative of cell death. When the exposure time is increased to 72 h the cells show a rounded shape morphology, with many cells were detached and floated in the growth medium, confirming the killing efficacy of the impregnated biodegradable ureteral stent against to T24 cancer cells. In the controls it is possible to see that the cells are normal confluent.

In an embodiment, biodegradable ureteral stents (non-degradable) were impregnated with four anti-cancer drugs (paclitaxel, epirubicin, doxorubicin and gemcitabine) by supercritical carbon dioxide (scCO2). The anti-cancer drugs were successfully impregnated into the biodegradable ureteral stents and the release was sustainable in an artificial urine solution. In all cases, when BUS was used as support a release of 100% of the impregnated drug was achieved after 72 h. In the case of the commercial stent the amount of drug impregnated was lower and the release was faster for all drugs, achieving 100% release within 24 h. The in vitro killing efficacy by direct contact with the anti-cancer biodegradable stents was similar for all the drugs tested. Our results indicate that the impregnated biodegradable ureteral stents developed may serve as carriers of anticancer drugs and potentially be an effective and sustained IDD system for upper tract urothelial carcinoma therapy.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable. The following claims further set out particular embodiments of the disclosure.

The following references, should be considered herewith incorporated in their entirety:

Aroso, I. M., Craveiro, R., Rocha, Â., Dionísio, M., Barreiros, S., Reis, R. L., Paiva, A., Duarte, A. R. C., 2015. Design of controlled release systems for THEDES-Therapeutic deep eutectic solvents, using supercritical fluid technology. Int. J. Pharm. 492, 73-9.

Audenet, F., Traxer, O., Bensalah, K., Rouprêt, M., 2013a. Upper urinary tract instillations in the treatment of urothelial carcinomas: A review of technical constraints and outcomes. World J. Urol. 31, 45-52.

Audenet, F., Yates, D. R., Cussenot, O., Rouprêt, M., 2013b. The role of chemotherapy in the treatment of urothelial cell carcinoma of the upper urinary tract (UUT-UCC). Urol. Oncol. 31, 407-13.

Babjuk, M., Burger, M., Zigeuner, R., Shariat, S. F., van Rhijn, B. W. G., Comperat, E., Sylvester, R. J., Kaasinen, E., Böhle, A., Palou Redorta, J., Rouprêt, M., 2013. EAU guidelines on non-muscle-invasive urothelial carcinoma of the bladder: update 2013. Eur. Urol. 64, 639-53.

Barros, A. A., Oliveira, C., Reis, R. L., Lima, E., Duarte, A. R. C., 2015a. Ketoprofen-eluting biodegradable ureteral stents by CO2 impregnation: In vitro study. Int. J. Pharm. 495, 651-9.

Barros, A. A., Rita, A., Duarte, C., Pires, R. A., Sampaio-Marques, B., Ludovico, P., Lima, E., Mano, J. F., Reis, R. L., 2015b. Bioresorbable ureteral stents from natural origin polymers. J. Biomed. Mater. Res. Part B Appl. Biomater. 103, 608-617.

Berens, A. R., Huvard, G. S., Korsmeyer, R. W., Kunig, F. W., 1992. Application of compressed carbon dioxide in the incorporation of additives into polymers. J. Appl. Polym. Sci. 46, 231-242.

Browne, S., Fontana, G., Rodriguez, B. J., Pandit, A., 2012. A protective extracellular matrix-based gene delivery reservoir fabricated by electrostatic charge manipulation. Mol. Pharm. 9, 3099-106.

Browne, S., Pandit, A., 2014. Multi-modal delivery of therapeutics using biomaterial scaffolds. J. Mater. Chem. B 2, 6692-6707.

Champeau, M., Thomassin, J.-M., Tassaing, T., Jerome, C., 2015. Drug Loading of Sutures by Supercritical CO2 Impregnation: Effect of Polymer/Drug Interactions and Thermal Transitions. Macromol. Mater. Eng. 300, 596-610.

Cooper, A. I., 2000. Polymer synthesis and processing using supercritical carbon dioxide. J. Mater. Chem. 10, 207-234.

D., L., M., M., M., K., M., S., 2014. Hydrogel based drug retention system for the treatment of upper tract urothelial carcinoma. Eur. Urol. Suppl. 13, e25-e25a.

Elvira, C., Fanovich, A., Fern??ndez, M., Fraile, J., San Rom??n, J., Domingo, C., 2004. Evaluation of drug delivery characteristics of microspheres of PMMA-PCL-cholesterol obtained by supercritical-CO 2 impregnation and by dissolution-evaporation techniques. J. Control. Release 99, 231-240.

Hadaschik, B. A., Ter Borg, M. G., Jackson, J., Sowery, R. D., So, A. I., Burt, H. M., Gleave, M. E., 2008. Paclitaxel and cisplatin as intravesical agents against non-muscle-invasive bladder cancer. BJU Int. 101, 1347-1355.

Hellenthal, N. J., Shariat, S. F., Margulis, V., Karakiewicz, P. I., Roscigno, M., Bolenz, C., Remzi, M., Weizer, A., Zigeuner, R., Bensalah, K., Ng, C. K., Raman, J. D., Kikuchi, E., Montorsi, F., Oya, M., Wood, C. G., Fernandez, M., Evans, C. P., Koppie, T. M., 2009. Adjuvant chemotherapy for high risk upper tract urothelial carcinoma: results from the Upper Tract Urothelial Carcinoma Collaboration. J. Urol. 182, 900-6.

JIAO, Z., CHEN, Z., WU, Y., MA, S., 2011. Determination of Paclitaxel Solubility in Carbon Dioxide Using Quartz Crystal Microbalance. Chinese J. Chem. Eng. 19, 227-231.

Kazarian, S. G., 2000. Polymer Processing with Supercritical Fluids. Polym. Sci. 42, 78-101.

Kazarian, S. G., Martirosyan, G. G., 2002. Spectroscopy of polymer/drug formulations processed with supercritical fluids: in situ ATR-IR and Raman study of impregnation of ibuprofen into PVP. Int. J. Pharm. 232, 81-90.

Khan, W., Farah, S., Domb, A. J., 2012. Drug eluting stents: developments and current status. J. Control. Release 161, 703-12.

Kikic, I., Sist, P., 2000. Applications of Supercritical Fluids to Pharmaceuticals: Controlled Drug Release Systems BT—Supercritical Fluids: Fundamentals and Applications, in: Kiran, E., Debenedetti, P. G., Peters, C. J. (Eds.). Springer Netherlands, Dordrecht, pp. 291-306.

Kikic, I., Vecchione, F., 2003. Supercritical impregnation of polymers. Curr. Opin. Solid State Mater. Sci. 7, 399-405.

Krambeck, A. E., Walsh, R. S., Denstedt, J. D., Preminger, G. M., Li, J., Evans, J. C., Lingeman, J. E., 2010. A Novel Drug Eluting Ureteral Stent: A Prospective, Randomized, Multicenter Clinical Trial to Evaluate the Safety and Effectiveness of a Ketorolac Loaded Ureteral Stent. J. Urol. 183, 1037-1043.

Lange, D., Bidnur, S., Hoag, N., Chew, B. H., 2015. Ureteral stent-associated complications[mdash] where we are and where we are going. Nat Rev Urol 12, 17-25.

Lu, S., Neoh, K. G., Kang, E.-T., Mahendran, R., Chiong, E., 2015a. Mucoadhesive polyacrylamide nanogel as a potential hydrophobic drug carrier for intravesical bladder cancer therapy. Eur. J. Pharm. Sci. 72, 57-68.

Lu, S., Neoh, K. G., Kang, E.-T., Mahendran, R., Chiong, E., 2015b. Mucoadhesive polyacrylamide nanogel as a potential hydrophobic drug carrier for intravesical bladder cancer therapy. Eur. J. Pharm. Sci. 72, 57-68.

Mendez-Probst, C. E., Goneau, L. W., MacDonald, K. W., Nott, L., Seney, S., Elwood, C. N., Lange, D., Chew, B. H., Denstedt, J. D., Cadieux, P. A., 2012. The use of triclosan eluting stents effectively reduces ureteral stent symptoms: a prospective randomized trial. BJU Int. 110, 749-754.

Munoz, J. J., Ellison, L. M., 2000. Upper tract urothelial neoplasms: incidence and survival during the last 2 decades. J. Urol. 164, 1523-1525.

NCCN, n.d. NCCN Clinical Practice Guidelines in Oncology (NCCN Guidelines®) Bladder Cancer.

Nunes, A. V, Rodriguez-Rojo, S., Almeida, A. P., Matias, A. A., Rego, D., Simplicio, A. L., Bronze, M. R., Cocero, M. J., Duarte, C. M. M., 2010. Supercritical fluids strategies to produce hybrid structures for drug delivery. J. Control. Release 148, e11-2.

Papadopoulos, E., Yousef, G., Scorilas, A., 2015. Gemcitabine impacts differentially on bladder and kidney cancer cells: distinct modulations in the expression patterns of apoptosis-related microRNAs and BCL2 family genes. Tumor Biol. 36, 3197-3207.

Pu, Y. S., Chen, J., Huang, C. Y., Guan, J. Y., Lu, S. H., Hour, T. C., 2001. Cross-resistance and combined cytotoxic effects of paclitaxel and cisplatin in bladder cancer cells. J. Urol. 165, 2082-5.

Sebaugh, J. L., 2011. Guidelines for accurate EC50/1050 estimation. Pharm. Stat. 10, 128-134.

Shaikh, M., Kichenadasse, G., Choudhury, N. R., Butler, R., Garg, S., 2013. Non-vascular drug eluting stents as localized controlled drug delivery platform: preclinical and clinical experience. J. Control. Release 172, 105-17.

Suleiman, D., Antonio Est??vez, L., Pulido, J. C., Garc??a, J. E., Mojica, C., 2005. Solubility of anti-inflammatory, anti-cancer, and anti-HIV drugs in supercritical carbon dioxide. J. Chem. Eng. Data.

Vandana, V., Teja, A. S., 1997. The solubility of paclitaxel in supercritical CO2 and N2O. Fluid Phase Equilib. 135, 83-87.

Yoda, S., Sato, K., Oyama, H. T., 2011. Impregnation of paclitaxel into poly(dl-lactic acid) using high pressure mixture of ethanol and carbon dioxide. RSC Adv. 1, 156-162.

York, P., Kompella, U. B., Shekunov, B. Y., 2004. Supercritical Fluid Technology for Drug Product Development, Drugs and the Pharmaceutical Sciences. Taylor & Francis.

Yu, Q., Zhang, J., Zhang, G., Gan, Z., 2015. Synthesis and Functions of Well-defined Polymer-drug Conjugates as Efficient Nanocarriers for Intravesical Chemotherapy of Bladder Cancera. Macromol. Biosci. 15, 509-520.

The invention claimed is:

1. A stent comprising a polymeric substrate, wherein the polymeric substrate comprises:
   10-50% (w/w) of alginate;
   45-85% (w/w) of gelatine;
   3-50% (w/w) a polymeric biodegradable resin for coating said polymeric substrate; and
   no more than 10% (w/w) of an anti-cancer drug;
   wherein at least one anti-cancer drug is selected from the list consisting of paclitaxel, epirubicin, doxorubicin, gemcitabine, and mixtures thereof.

2. The stent according to claim 1, comprising no more than 5% (w/w) of the anti-cancer drug.

3. The stent according to claim 1, wherein the anti-cancer drug comprises a mixture of anti-cancer drugs, wherein the mixture is: paclitaxel and epirubicin; or paclitaxel and doxorubicin; or paclitaxel and gemcitabine; or epirubicin and doxorubicin; or epirubicin and gemcitabine; or doxorubicin and gemcitabine; or paclitaxel, epirubicin and doxorubicina; or epirubicin, doxorubicina and gemcitabine; or paclitaxel, epirubicin and gemcitabine.

4. The stent according to claim 1, wherein the polymeric substrate comprises 20-40% (w/w) of alginate and 55-70% (w/w) of gelatine.

5. The stent according to claim 1, further comprising a contrast agent.

6. The stent according to claim 5, comprising:
   2-5% (w/w) of the contrast agent, wherein the polymeric substrate comprises 20-40% (w/w) of alginate and 55-70% (w/w) of gelatine.

7. The stent according to claim 1, further comprising:
   5% (w/w) of a contrast agent, wherein the polymeric substrate comprises 30% (w/w) of alginate and 65% (w/w) of gelatine.

8. The stent according to claim 1, wherein said resin is selected from the group consisting of: polycaprolactone resin, polyglycolide and its copolymers, poly(lactic-co-glycolic acid) with lactic acid, poly(glycolide-co-caprolactone) with ε-caprolactone, and poly (glycolide-co-trimethylene carbonate) with trimethylene carbonate, or mixtures of the foregoing.

9. The stent according to claim 1, further comprising contrast agent is selected from the group consisting of: barium salts, bismuth salts, spinel pigments, or mixtures of the foregoing.

10. The stent according to claim 1, further comprising a crosslinking agent.

11. The stent according to claim 10, further comprising a crosslinking agent is selected from the ionic crosslinking agents, including ionic crosslinking agents having monovalent or divalent ions, from which:
   the cation is selected from the group consisting of: calcium, magnesium, barium, strontium, boron, beryllium, aluminium, iron, copper, cobalt, lead, silver, or mixtures of the foregoing;
   the anion is selected from the group consisting of: chloride, nitrate, phosphate, citrate, borate, succinate, maleate or oxalate, or mixtures of the foregoing.

12. The stent according to claim 1, further comprising a second anti-cancer drug selected from the group consisting of: methotrexate, vinblastine, cisplatin, granulocyte colony-stimulating factor, carboplatin, 5-fluorouracil, ifosfamide, pemetrexed, mitomycin C, capecitabine, Bacillus Calmette-Guerin (BCG) or mixtures of the foregoing.

13. The stent according to claim 1, further comprising an anti-inflammatory agent, an anti-microbial agent, an antiviral agent, or mixtures of the foregoing.

14. The stent according to claim 1, wherein the anti-cancer drug is impregnated in the stent by supercritical fluid $CO_2$.

15. A ureteral stent comprising a polymeric substrate, wherein the polymeric substrate comprises:
   10-50% (w/w) of alginate;
   45-85% (w/w) of gelatine;

a polymeric biodegradable resin for coating said polymeric substrate; and no more than 10% (w/w) of an anti-cancer drug.

16. A composition for use in human medicine or veterinary, comprising alginate, gelatine, a polymeric biodegradable resin and no more than 5% (w/w) of an anti-cancer drug, wherein said composition is administrated in a biodegradable stent, wherein said stent comprises 10-50% (w/w) of alginate, 45-85% (w/w) of gelatine, a polymeric biodegradable resin for coating said polymeric substrate, and said no more than 5% (w/w) of the anti-cancer drug.

17. The composition of claim 16, comprising no more than 4.95% (w/w) of the anti-cancer drug.

18. The composition of claim 16, wherein the anti-cancer drug comprises at least one anti-cancer drug selected from the group consisting of: paclitaxel, epirubicin, doxorubicin, gemcitabine, or mixtures of the foregoing.

* * * * *